US011085907B2

(12) United States Patent
Rao

(10) Patent No.: US 11,085,907 B2
(45) Date of Patent: Aug. 10, 2021

(54) SYSTEM AND METHOD FOR DETECTING CONTAMINANTS IN WATER

(71) Applicant: Gitanjali Adhikarla Rao, Lone Tree, CO (US)

(72) Inventor: Gitanjali Adhikarla Rao, Lone Tree, CO (US)

( * ) Notice: Subject to any disclaimer, the term of this patent is extended or adjusted under 35 U.S.C. 154(b) by 163 days.

(21) Appl. No.: 16/212,591

(22) Filed: Dec. 6, 2018

(65) Prior Publication Data
US 2019/0170721 A1 Jun. 6, 2019

Related U.S. Application Data

(60) Provisional application No. 62/747,067, filed on Oct. 17, 2018, provisional application No. 62/595,477, filed on Dec. 6, 2017.

(51) Int. Cl.
G01N 33/18 (2006.01)
G01N 27/06 (2006.01)
G08B 5/22 (2006.01)
B82Y 15/00 (2011.01)
H04Q 9/02 (2006.01)
G08B 21/12 (2006.01)
H04Q 9/00 (2006.01)

(52) U.S. Cl.
CPC ......... *G01N 33/1886* (2013.01); *G01N 27/06* (2013.01); *G08B 5/22* (2013.01); *G08B 21/12* (2013.01); *H04Q 9/00* (2013.01); *H04Q 9/02* (2013.01); *B82Y 15/00* (2013.01); *H04Q 2209/40* (2013.01); *H04Q 2209/43* (2013.01); *H04Q 2209/84* (2013.01); *H04Q 2209/86* (2013.01)

(58) Field of Classification Search
CPC ...... G01N 33/1886; G01N 27/06; G08B 5/22; G08B 21/12; H04Q 9/00; H04Q 9/02; H04Q 2209/40; H04Q 2209/43; H04Q 2209/84; H04Q 2209/86; B82Y 15/00
See application file for complete search history.

(56) References Cited

U.S. PATENT DOCUMENTS

2007/0132043 A1* 6/2007 Bradley ................. B82Y 10/00
257/414
2007/0168145 A1* 7/2007 Beyer .................... C12Q 1/006
702/85

(Continued)

*Primary Examiner* — Tung X Nguyen
*Assistant Examiner* — Feba Pothen
(74) *Attorney, Agent, or Firm* — Lewis Roca Rothgerber Christie LLP

(57) ABSTRACT

Devices, systems, and methods for detecting contaminants in water are provided. A device may include: a sensor configured to detect one or more contaminants in a liquid when the sensor is dipped into the liquid; a computing device connected to the sensor, the computing device being configured to determine a resistance of the device when the sensor is dipped into the liquid; and a wireless electronic device connected to the computing device via one or more wireless links and configured to receive the resistance of the device when the sensor is dipped into the liquid from the computing device, and the wireless electronic device determines a level of contamination in the liquid based on a difference between the resistance of the device when the sensor is dipped into the liquid and a set or predetermined resistance.

20 Claims, 10 Drawing Sheets

(56) References Cited

U.S. PATENT DOCUMENTS

| 2016/0167966 A1* | 6/2016 | Hocke | H01M 4/96 |
| | | | 134/28 |
| 2017/0323108 A1* | 11/2017 | Mehta | G06F 21/6245 |
| 2018/0031504 A1* | 2/2018 | Ricci | G01N 33/22 |

* cited by examiner

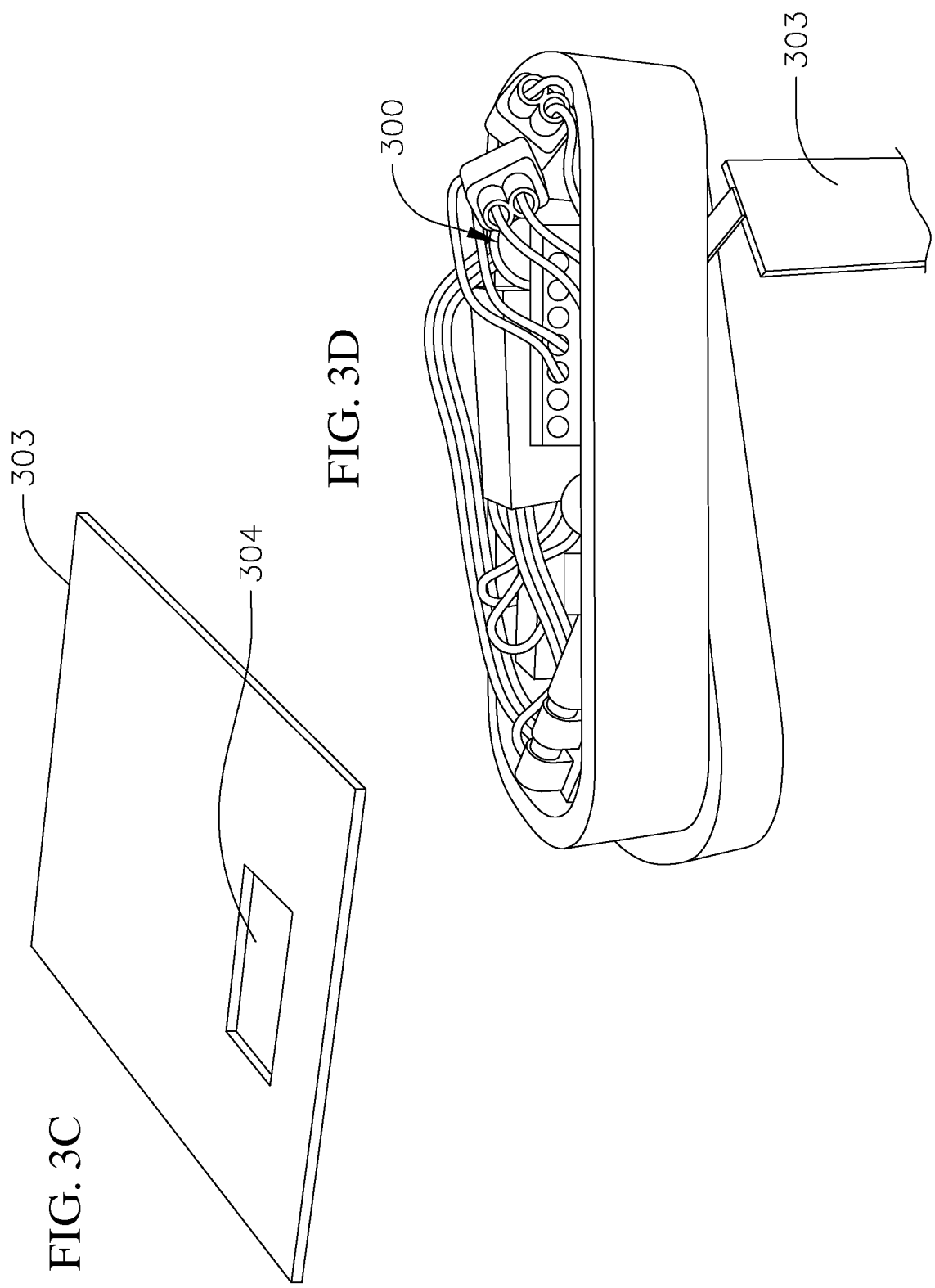

SYSTEM AND METHOD FOR DETECTING
CONTAMINANTS IN WATER

CROSS-REFERENCE TO RELATED APPLICATION(S)

The present application claims priority to and the benefits of U.S. Provisional Patent Application Ser. No. 62/595,477, filed Dec. 6, 2017 and 62/747,067, filed Oct. 17, 2018 and both entitled "LEAD AND LEAD COMPOUND DETECTION IN WATER USING CARBON NANOTUBE SENSOR," the entire contents of which are hereby expressly incorporated by reference.

FIELD

One or more aspects of embodiments according to the present invention relate to contaminants detection in water, for example, a system and method for detecting contaminants in water.

BACKGROUND

Contamination of the domestic water supplies may be a serious and growing global problem. Therefore, there is a need for a reliable, time efficient and cost effective system to detect contaminants in domestic water supplies.

The above information disclosed in this Background section is only for enhancement of understanding of the background of the invention and therefore it may contain information that does not constitute prior art.

SUMMARY

This summary is provided to introduce a selection of features and concepts of embodiments of the present disclosure that are further described below in the detailed description. This summary is not intended to identify key or essential features of the claimed subject matter, nor is it intended to be used in limiting the scope of the claimed subject matter. One or more of the described features may be combined with one or more other described features to provide a workable device.

Aspects of example embodiments of the present disclosure relate to devices, systems, and methods for detecting contaminants (e.g., lead and lead based compounds) in water.

According to one or more embodiments, a device includes: a sensor configured to detect one or more contaminants in a liquid when the sensor is dipped into the liquid; a computing device connected to the sensor, the computing device being configured to determine a resistance of the device when the sensor is dipped into the liquid; and a wireless electronic device connected to the computing device via one or more wireless links and configured to receive the resistance of the device when the sensor is dipped into the liquid from the computing device, and the wireless electronic device determines a level of contamination in the liquid based on a difference between the resistance of the device when the sensor is dipped into the liquid and a set or predetermined resistance.

According to one or more embodiments, a method for detecting contaminants in a liquid includes: submerging a sensor connected to a device into a liquid; determining, using a processor in the device, a resistance of the device when the sensor is submerged into the liquid; determining, at a wireless electronic device connected to the processor via one or more wireless links, a difference between the resistance of the device when the sensor is submerged into the liquid and a set or predetermined resistance, based on the determined resistance of the device received from the processor; and determining a level of contamination in the liquid based on the difference between the resistance of the device when the sensor is submerged into the liquid and the set or predetermined resistance.

According to one or more embodiments, a system includes: a carbon nanotube sensor configured to detect one or more contaminants in a liquid when the carbon nanotube sensor is submerged into the liquid, wherein each of one or more carbon nanotubes in the carbon nanotube sensor is doped with one of chloride ions, iodide ions, or fluoride ions; a microcontroller connected to the carbon nanotube sensor via one or more resistors, wherein the microcontroller is configured to determine a resistance of the system when the carbon nanotube sensor is submerged into the liquid, using the one or more resistors; and a wireless electronic device connected to the microcontroller via one or more wireless links and configured to receive the resistance of the system when the carbon nanotube sensor is submerged into the liquid from the microcontroller, wherein the wireless electronic device determines a level of contamination in the liquid based on a difference between the resistance of the system when the carbon nanotube sensor is submerged into the liquid and a set or predetermined resistance.

BRIEF DESCRIPTION OF THE DRAWINGS

These and other features of some example embodiments of the present invention will be appreciated and understood with reference to the specification, claims, and appended drawings, wherein:

FIGS. 3A-3D illustrate different parts of a device to detect contaminants (e.g., lead or lead compounds) in water;

DETAILED DESCRIPTION

Figure 1:
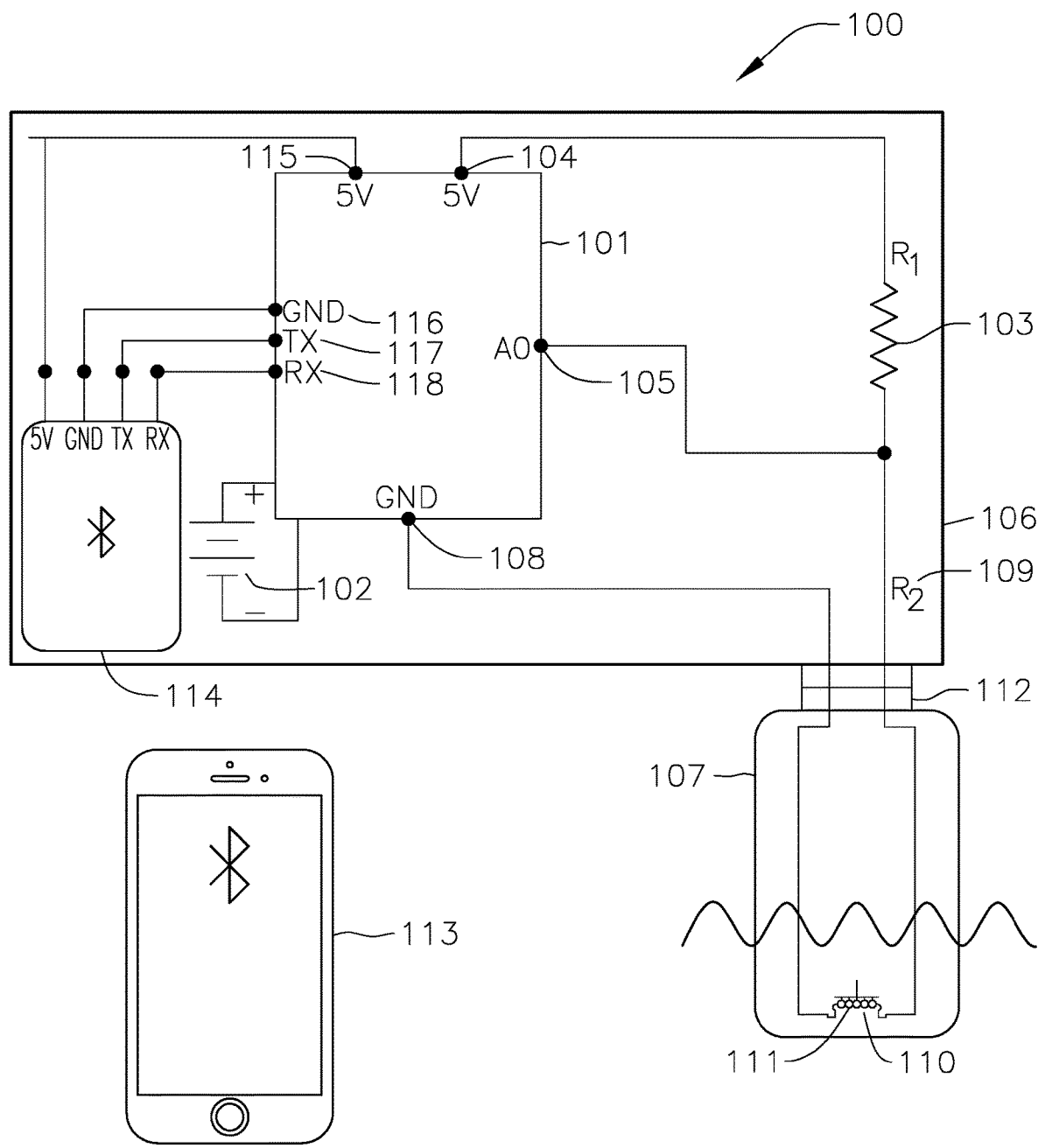
FIG. 1 illustrates a device 100 to detect contaminants (e.g., lead or lead compounds) in water.

The detailed description set forth below in connection with the appended drawings is intended as a description of some example embodiments of a system and method for detecting contaminants (e.g., lead and lead based compounds) in water provided in accordance with the present invention and is not intended to represent the only forms in which the present invention may be constructed or utilized. The description sets forth the features of the present invention in connection with the illustrated embodiments. It is to be understood, however, that the same or equivalent functions and structures may be accomplished by different embodiments that are also intended to be encompassed within the scope of the invention. As denoted elsewhere herein, like element numbers are intended to indicate like elements or features.

Contamination (e.g., lead contamination) of the domestic water supplies may be a serious and growing global problem. Systems and methods currently available in the market for detecting contaminants (e.g., lead or lead based compounds) in domestic water supply may use test strips for instant detection or may require the consumer to collect and ship the sample (e.g., water) to a test facility or a laboratory for processing. The detection of contaminants (e.g., lead or lead based compounds) using the test strips for instant results may be inaccurate. Also, conducting the test for contaminant (e.g., lead) detection at a laboratory facility may be expensive and time consuming. Therefore, there is a need for a user friendly, reliable, time efficient, and cost effective system and method to detect contaminants (e.g., lead or lead based compounds) in domestic water supply.

One or more example embodiments of the present disclosure provides a system and method for detecting contaminants (e.g., lead or lead based compounds) in water using carbon nanotubes. The one or more example embodiments of the present disclosure provide a fast, user friendly, and cost effective detection of contaminants (e.g., lead and lead compounds) in water with an accurate result.

The one or more example embodiments of the present disclosure may provide a device to instantly detect the presence of contaminants (e.g., lead compounds) in water, map the level of contaminant to a scale that classifies the contaminant (e.g., lead) level as "safe", "moderate risk", and "unsafe", and then send the results to a display module of a wireless device using a wireless communication link, for example, cellular communication, Wi-Fi, Bluetooth Low Energy (LE), or the like. In some example embodiments, one or more wireless devices, connected to the device for detecting contaminants (e.g., lead or lead compounds) in water, may receive the results (e.g., "safe", "moderate risk", and "unsafe"), via wireless communication, as soon as the test is completed. In some example embodiment, a custom mobile application may be installed in one or more wireless devices to easily access the test results in a user friendly visual scale (e.g., "safe", "moderate risk", and "unsafe") from the device for detecting contaminants (e.g., lead or lead compounds) in water, via wireless communication.

FIG. 1 illustrates an example device 100 wirelessly connected to a wireless device 113. The device 100 may be used to instantly detect contaminants (e.g., lead or lead compounds) in water.

Device 100 includes a microcontroller 101, a battery source 102 to power the microcontroller 101, a first resistor 103 connected between a 5V output pin 104 of the microcontroller 101 and an analog input or digital I/O A0 pin 105 of the microcontroller 101. The device 100 also includes a wireless (e.g., Bluetooth) transmitter/receiver 114 connected to the microcontroller 101 at a 5V input pin 115, a ground pin GND 116, a pin 117 for transmission of the data, and a pin 118 to receive data. The device 100 further includes a housing 106 to contain the microcontroller 101, the battery source 102, the wireless transmitter/receiver 114, and the first resistor 103.

In some example embodiments, the microcontroller 101 may be an Adafruit Feather 32u4 Bluefruit microcontroller, with ports (A0 to A5) for input of digital and analog data, built in Bluetooth LE (e.g., 114) and 4.3V power source (e.g., 102). In some example embodiments, any processor or computing device with wireless connectivity may be used instead of the microcontroller 101. The battery source 102 may be a 4.3V, 100 mA Lithium Polymer or Lithium Ion battery source. The value of the first resistor 103 may be known, which may be used to calculate the change in resistance or current in the device 100.

The device 100 also includes a sensing device 107. The sensing device 107 may be located outside the housing 106 and may be connected to the microcontroller 101 via a small opening 112 at the bottom of the housing 106. The sensing device 107 may be connected between a ground terminal GND 108 and the analog input or digital I/O A0 pin 105 of the microcontroller 101. In some example embodiments, the sensing device 107 may be connected to the analog input or digital I/O A0 pin 105 of the microcontroller 101 via a second resistor 109. In some example embodiments, the second resistor 109 may be located inside the housing 106. The sensing device 107 may be an insulated cartridge with a small opening 110 at the bottom of the sensing device 107 to expose a sensor 111. The sensor 111 may be a carbon nanotube sensor doped with chloride ions, which may be exposed to air or liquid through the opening in the insulated cartridge or sensing device 107.

In some example embodiments, the microcontroller 101 in device 100 may instantly detect the presence of contaminants (e.g., lead compounds) in water, map to a scale that classifies the contaminant (e.g., lead) levels as "safe", "moderate risk", and "unsafe", and then send the results to a display module of a wireless device 113 connected to the device 100 via a wireless communication link (e.g., Wi-Fi, Bluetooth, or the like), as soon as the test is completed.

In some example embodiments, during the operation of device 100, when the carbon nanotube-based sensor 111 is dipped in a contaminated water, the contaminants (e.g., lead compounds) in water, such as lead acetate, react with the chloride ions in the carbon nanotubes of the sensor 111, forming lead chloride molecules in the carbon nanotubes of the sensor 111. With the addition of these molecules (e.g., lead acetate) in the carbon nanotubes of the sensor 111, the effective resistance of the circuit of device 100 increases. The new resistance (e.g., the resistance of device 100 when the sensor 111 is dipped in a contaminated water) of the circuit of device 100 may be calculated by the microcontroller 101 using the first resistor 103. The first resistor 103 may act as a multimeter coded into the microcontroller 101, and may be calibrated on scale of the contaminant (e.g., lead acetate) in the water.

In some example embodiments, the wireless device 113 (e.g., smart phones, tablets, computers, or the like), connected to the device 100 via a wireless communication link (e.g., Wi-Fi, Bluetooth, or the like), may receive the new resistance of the device 100, as soon as the new resistance is calculated by the microcontroller 101. The data regarding the new resistance of the device 100 may be stored in the local memory of the wireless device 113, or may be stored in a remote server or a cloud server connected to the wireless device 113.

In some example embodiments, the wireless device 113 may read and interpret the data received from the device 100 with respect to the new resistance of the device 100, via a custom application installed at the wireless device 113. For example, the wireless device 113 may compare the resistance of the device 100 when the sensor 111 is not dipped into the water (e.g., may be stored in the memory of the wireless device 113) with the new resistance of the device 100 when the sensor 111 is dipped in the contaminated (e.g., lead contaminated) water, and determine the difference in resistance. If the difference (e.g., y) is less than or equal to a first threshold (e.g., x1) (e.g., y≤x1), the application may conclude that the amount of contamination (e.g., lead contamination) in the water is "safe" for drinking purposes and may display "safe" in the display of the wireless device 113. If the difference (e.g., y) is more than the first threshold (e.g., x1) but less than or equal to a second threshold (e.g., x2) (e.g., x1<y≤x2), the application may conclude that the amount of contamination (e.g., lead contamination) in the water is at "moderate risk" for drinking purposes and may display "moderate risk" in the display of the wireless device 113. However, if the difference (e.g., y) is more than the second threshold (e.g., y>x2), the application may conclude that the amount of contamination (e.g., lead contamination) in the water is "unsafe" for drinking purposes and may display "unsafe" in the display of the wireless device 113.

In some example embodiments, the custom application installed at the wireless device 113 may allow the user conducting the test for detecting the amount of contaminant (e.g., lead) in the water to upload the time, location, and status of the test onto a public database. The information in the database may be compiled and uploaded into a heat map showing lead levels in various locations in matter of seconds.

In some example embodiments, all the components (e.g., microcontroller 101, battery source 102, first resistor 103, sensor 107, the wireless transmitter/receiver 114, and the second resistor 109) of the device 100 of FIG. 1, may be fabricated into as single compact circuit board, making the device 100 small and robust. Also, the device 100 may be produced using 3D printing as a nylon-based device. The device 100 may also be produced as at scale molded plastic device.

In some example embodiments, the device 100 may be used for sensing various types of contaminants in the liquids by using a sensor (and software code of the microcontroller 101) compatible for detecting the contaminant being tested. For example, a carbon nanotube sensor doped with ions that react to the new contaminant that is being tested may be used instead of the carbon nanotube sensor 111 doped with chloride ions used to detect lead contaminants. An example might be carbon nanotube sensor 111 doped with fluoride ions used to detect mercury contamination.

In some example embodiments, to test for new contaminants, software changes may be needed in the microcontroller 101 and the application stored in the wireless device 113. For example, the microcontroller code where the detection and calibration happens, may be re-coded for a different resistance threshold. The application code (in the wireless device 113) may be changed to use a new scale to display results, depending on the contaminant.

Figure 2:
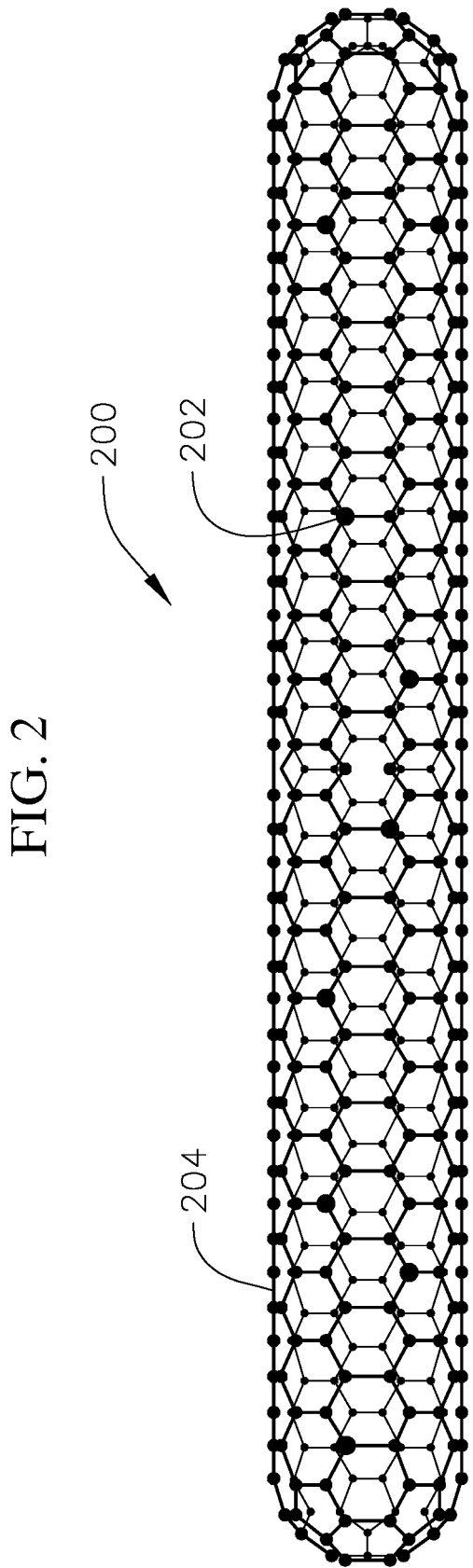
FIG. 2 illustrates a chloride doped single walled carbon nanotube.

FIG. 2 illustrates a chloride doped single walled carbon nanotube 200. The carbon nanotube 200 may be the sensor 111 of FIG. 1. FIG. 2 also illustrates chloride ions 202 in a single walled (e.g., bucky paper) carbon nanotube 200 and a single walled armchair (e.g., bucky paper) design 204 of the carbon nanotube 200. The length of bucky paper carbon nanotube 200 may change depending on the application. In the exemplary embodiment of FIG. 2, the amount of chloride dopant in the carbon nanotube 200 may be 5%. However, different percentage of the chloride dopant may be used. Also, in some example embodiments, iodide or fluoride dopant may be used to accomplish the same functionality as achieved from the chloride dopant.

Figure 3A:
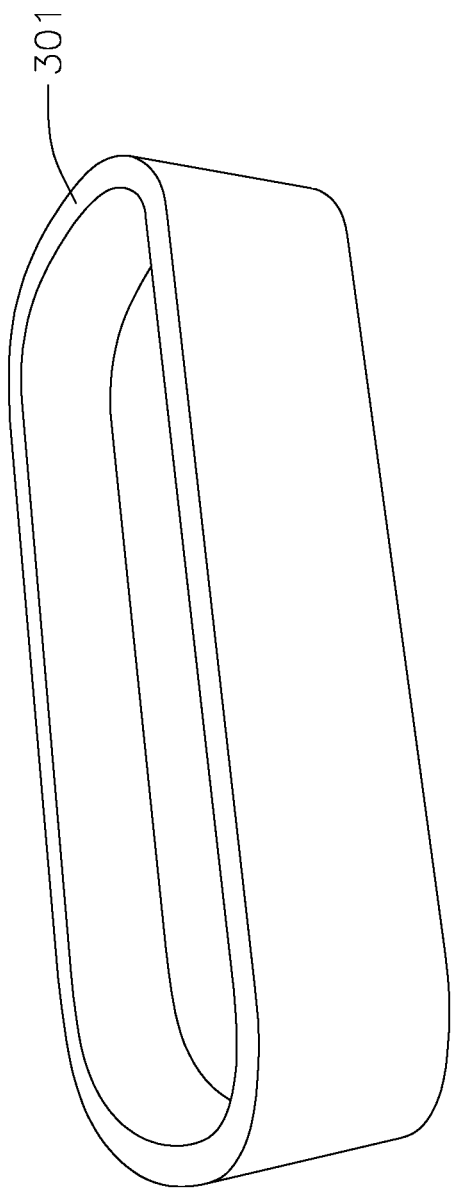
Figure 3B:
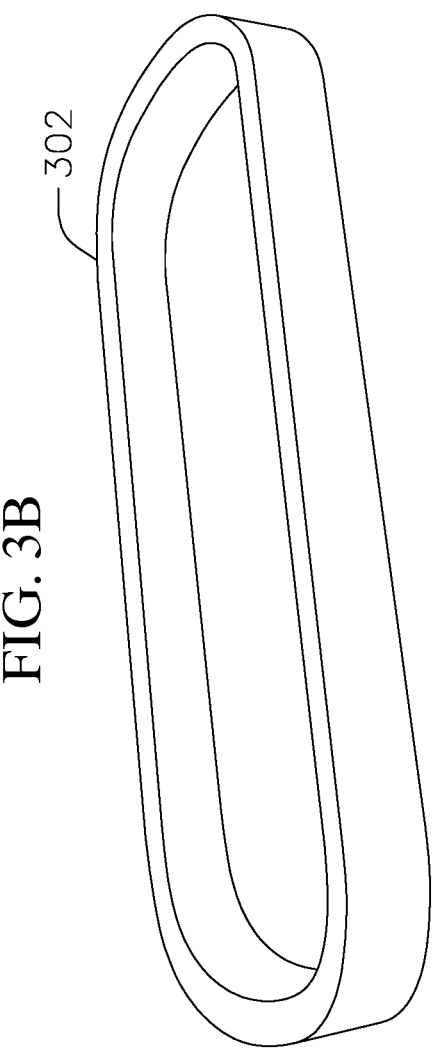

FIGS. 3A-3D illustrate different parts of a device 300. Device 300 may be the device 100 of FIG. 1. In FIG. 3A, a housing 301 may house different components (e.g., microcontroller 101, battery source 102, first resistor 103, the wireless transmitter/receiver 114, and the second resistor 109) of the device 300. The housing 301 may be the housing 106 of FIG. 1. FIG. 3B illustrates a device cover 302 to completely enclose the different electronic components (e.g., microcontroller 101, battery source 102, first resistor 103, the wireless transmitter/receiver 114, and the second resistor 109) of the device 300 in the housing 301 and protect the electronic components of device 300 inside the housing 301 from damage. FIG. 3C illustrates an insulated cartridge 303 with a small opening 304 to expose a carbon nanotube sensor. The insulated cartridge 303 may be the sensing device 107 of FIG. 1. The insulated cartridge 303 may have a small opening 304 at the bottom of the insulated cartridge 303 to expose the carbon nanotube sensor (e.g., sensor 111 of FIG. 1) doped with chloride ions, to the water. FIG. 3D illustrates device 300 with the cartridge 303 inserted at the bottom of the device 300.

Figure 4:
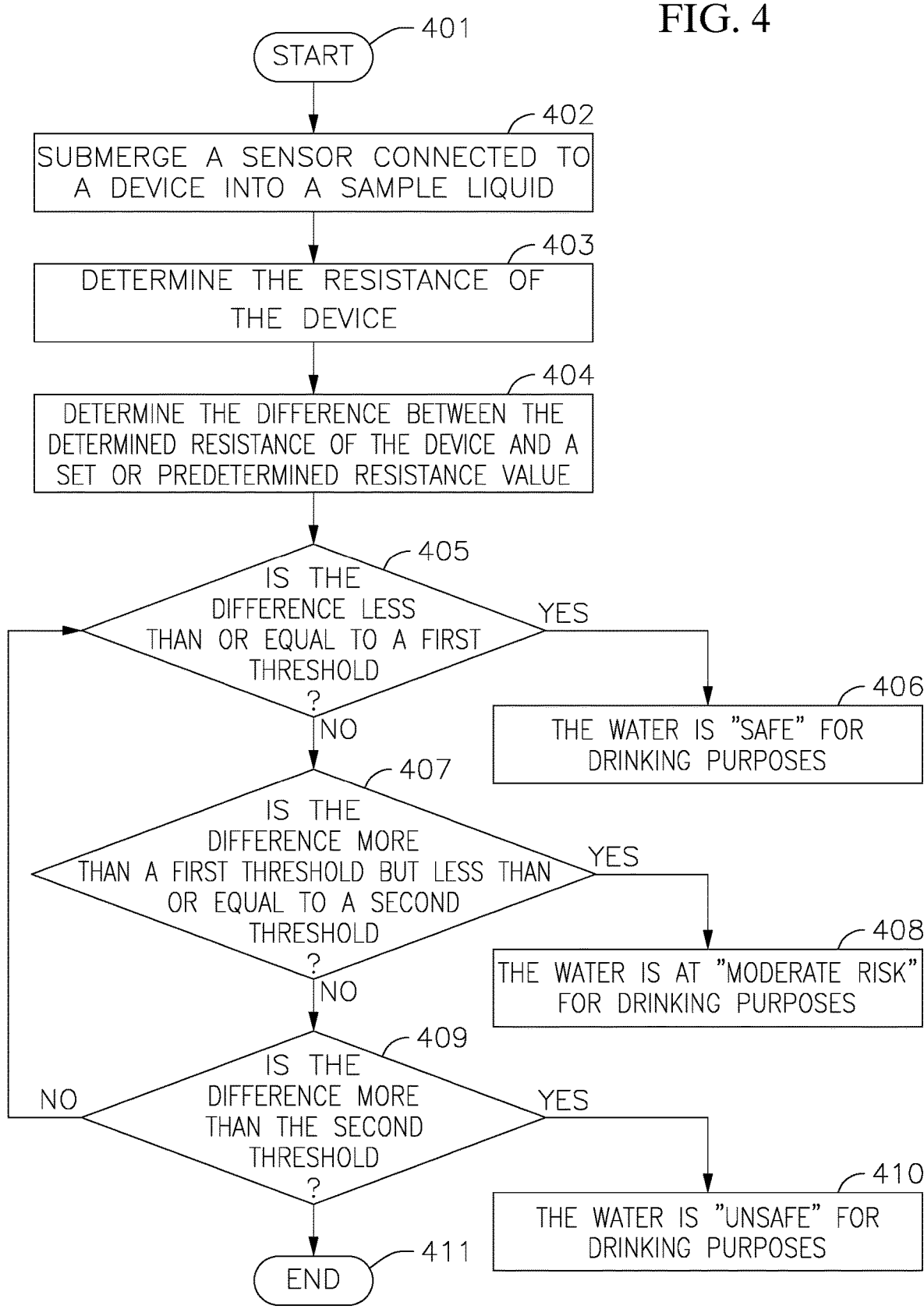
FIG. 4 illustrates a method for detecting contaminants (e.g., lead and lead based compounds) in water.

FIG. 4 illustrates a method for detecting contaminants (e.g., lead and lead based compounds) in water. The method may be performed using the assembly of device 100 and the wireless device 113.

At 402, a sensor connected to the device 100 may be submerged into a sample water to measure the amount of contamination (e.g., lead contamination) in the sample water. The sensor may be the carbon nanotube-based sensor 111 of FIG. 1. The carbon nanotube-based sensor 111 may be doped with chloride ions and when the carbon nanotube-based sensor 111 is dipped in a contaminated (e.g., lead contaminated) water, the contaminants (e.g., lead compounds) in the water such as lead acetate, react with the chloride ions in the sensor 111, forming lead chloride molecules in the carbon nanotubes of the sensor 111. With the addition of these molecules (e.g., lead acetate) in the carbon nanotubes of the sensor 111, the effective resistance of the circuit of device 100 increases.

At 403, a computing device, for example, the microcontroller 101 may determine the resistance of the device 100 when the carbon nanotube-based sensor 111 is dipped into the water, using the first resistor 103.

At 404, the difference between the resistance of the device 100 when the carbon nanotube-based sensor 111 is dipped into the water and a set or predetermined resistance value (e.g., the resistance of device 100 without the sensor 111 being dipped into the water, which may be stored in the memory of the wireless device 113) may be determined using the custom application installed in the wireless device 113.

At 405, the wireless device 113, using the custom application, determines if the difference between the resistance values determined at 404 is less than or equal to a first threshold. If the difference (e.g., y) between the resistance values is less than or equal to the first threshold (e.g., x1) (e.g., y≤x1), at 406, the wireless device 113 may conclude that the amount of contaminant (e.g., lead) in the water is "safe" for drinking purposes and may display "safe" in the display of the wireless device 113. Otherwise, at 407, the wireless device 113, using the custom application, determines if the difference (e.g., y) is more than the first threshold (e.g., x1) but less than or equal to a second threshold (e.g., x2) (e.g., x1<y≤x2). If so, at 408, the wireless device 113 may conclude that the amount of contaminant in the water is "moderate risk" for drinking purposes and may display "moderate risk" in the display of the wireless device 113. However, at 407, if the wireless device 113, using the custom application, determines that the difference (e.g., y) is more than the first threshold (e.g., x1) but not less than or equal to the second threshold, at 409, the wireless device 113 determines if the difference (e.g., y) is more than the second threshold (e.g., y>x2). If so, at 410, the wireless device 113 may conclude that the amount of contaminant (e.g., lead) in the water is "unsafe" for drinking purposes and may display "unsafe" in the display of the wireless device 113.

Figure 5:
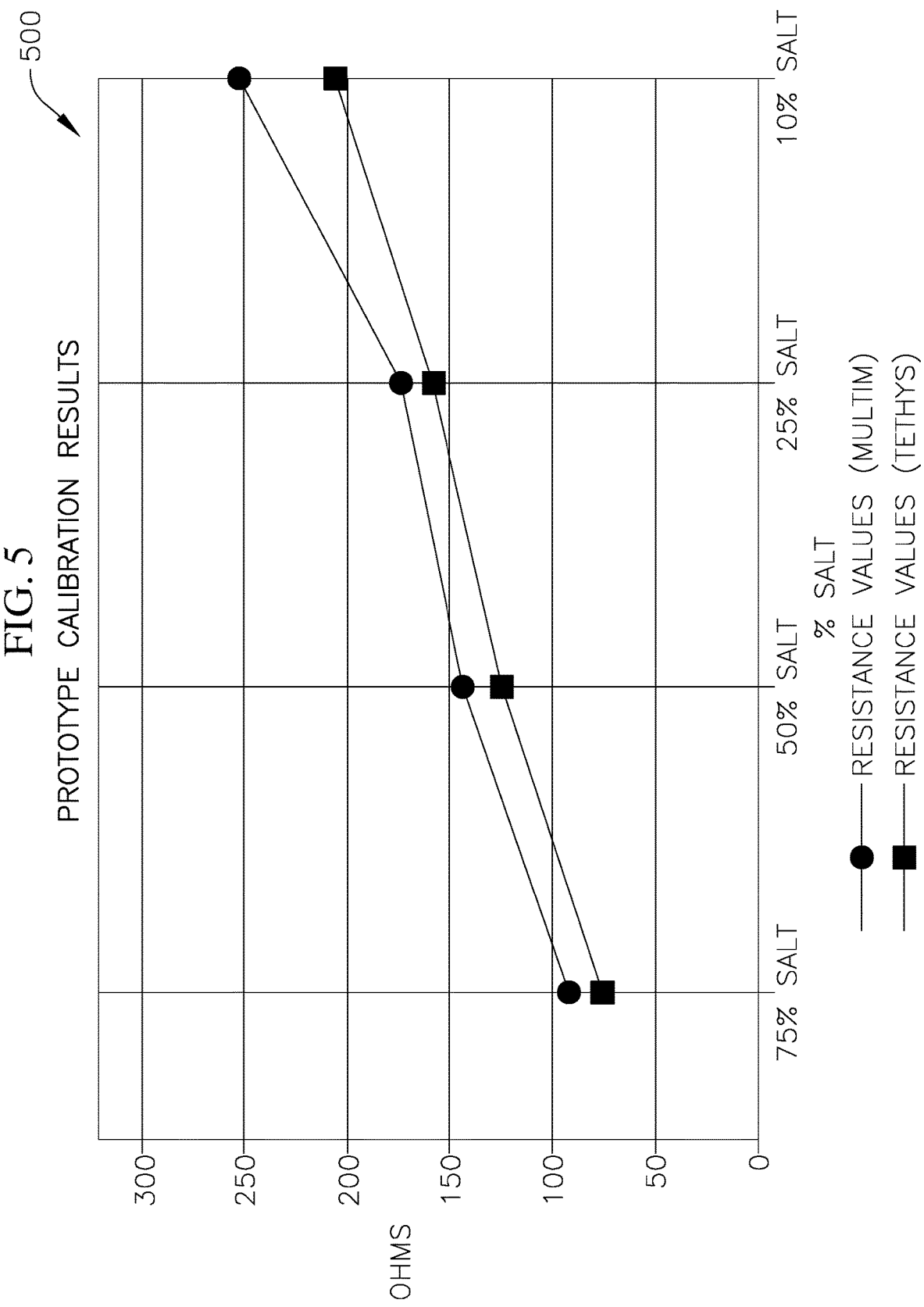
FIG. 5 illustrates the multimeter calibration of the device of FIG. 1 and a commercial multimeter.

FIG. 5 illustrates the comparison of the resistance values of the second resistor 109 of FIG. 1 to a commercial multimeter resistance values when the sensor 111 is submerged into different percentages of salt solutions (e.g., 75% salt, 50% salt, 25% salt, 10% salt). As the concentration of salt decreased, the resistance values of both the second resistor 109 of FIG. 1 and the commercial multimeter increased. The second resistor 109 of FIG. 1 had a 10-20% error margin to the commercial multimeter. This tests helped calibrate the multimeter ensuring accurate resistance values and results.

Figure 6:
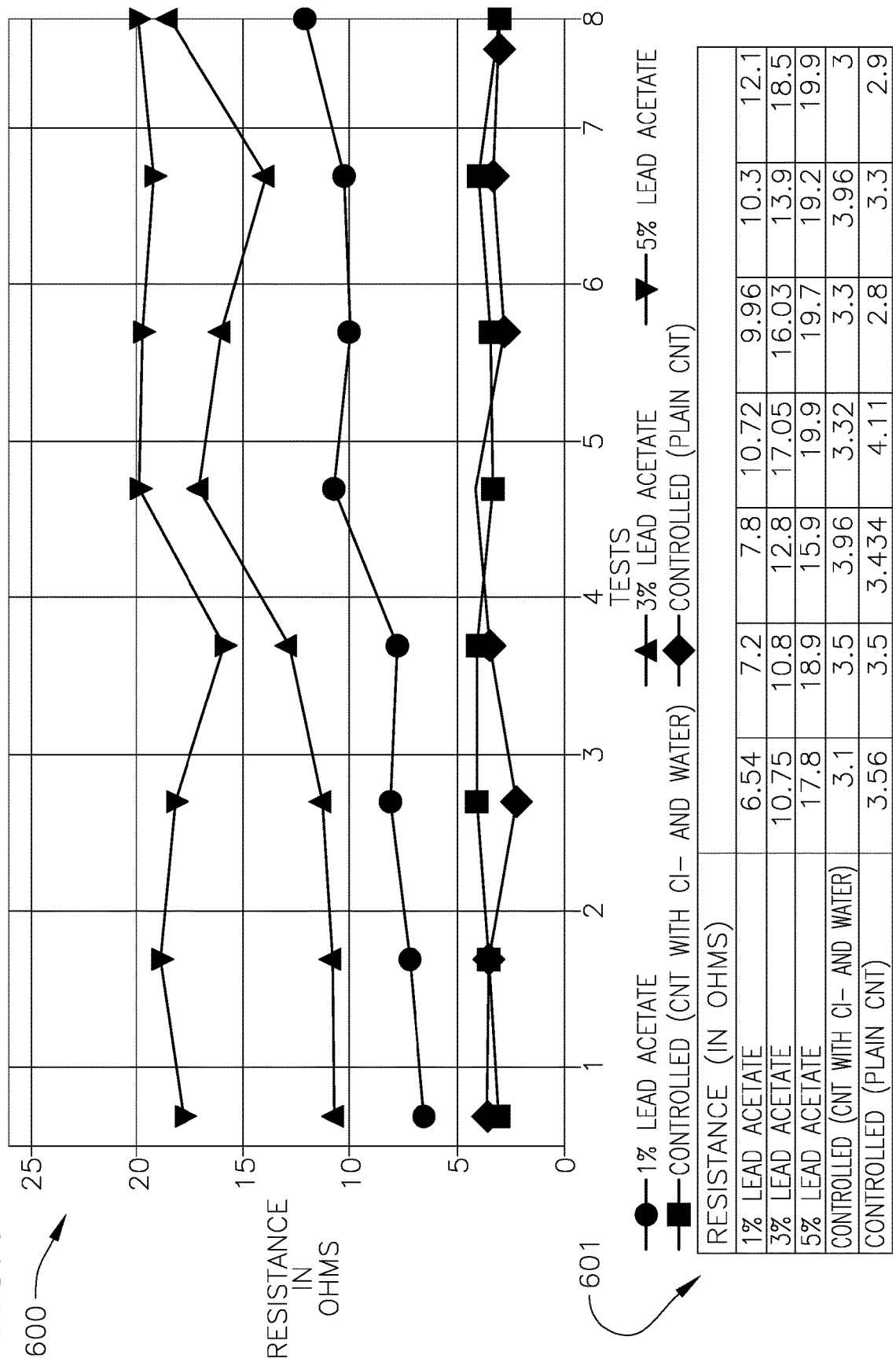
FIG. 6 illustrates the resistance values of the device of FIG. 1 with different concentrations of lead.

FIG. 6 illustrates the resistance values of the device 100 of FIG. 1 when the sensor 111 is submerged into a lead contaminated liquid. As shown in FIG. 6, the resistance of the device 100 is directly proportional to the percentage of lead contamination in the water, as the resistance of the device 100 is highest (e.g., between 15 ohms and 20 ohms) with the highest (e.g., 5%) concentration of the contaminant lead acetate in the liquid and the resistance of the device 100 is lowest (e.g., between 7 ohms and 13 ohms) with the lowest (e.g., 1%) concentration of the contaminant lead acetate in the liquid.

Figure 7:
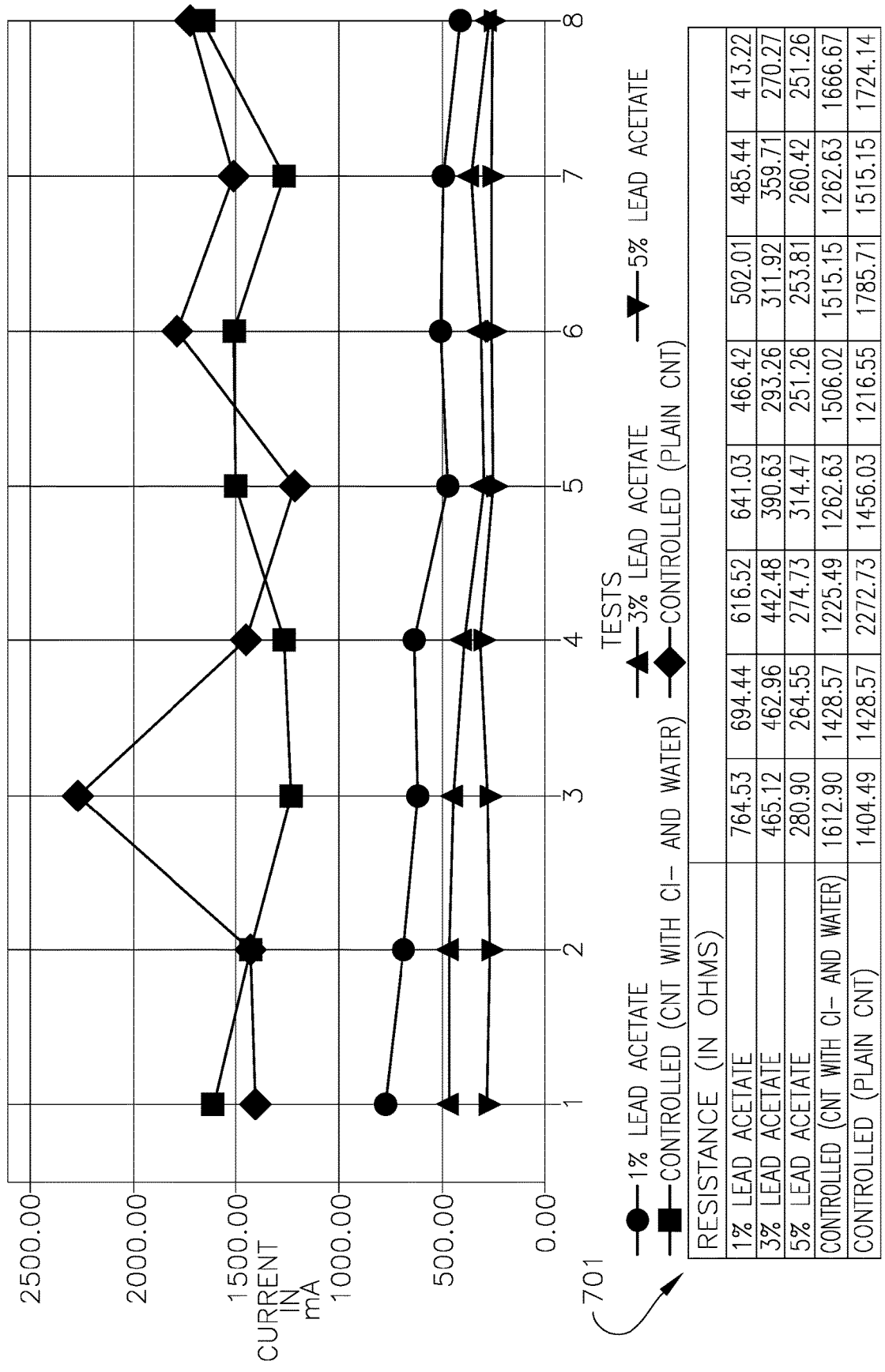
FIG. 7 illustrates the current values in the device of FIG. 1 with different concentrations of lead.

FIG. 7 illustrates the current values in the device 100 of FIG. 1 when the sensor 111 is submerged into a lead contaminated liquid. As shown in FIG. 7, the current flowing through the device 100 is inversely proportional to the percentage of lead contamination in the water, as the current values of the device 100 is highest with the lowest (e.g., 1%) concentration of the contaminant lead acetate in the liquid and the current values of the device 100 is lowest with the highest (e.g., 5%) concentration of the contaminant lead acetate in the liquid.

Figure 8:
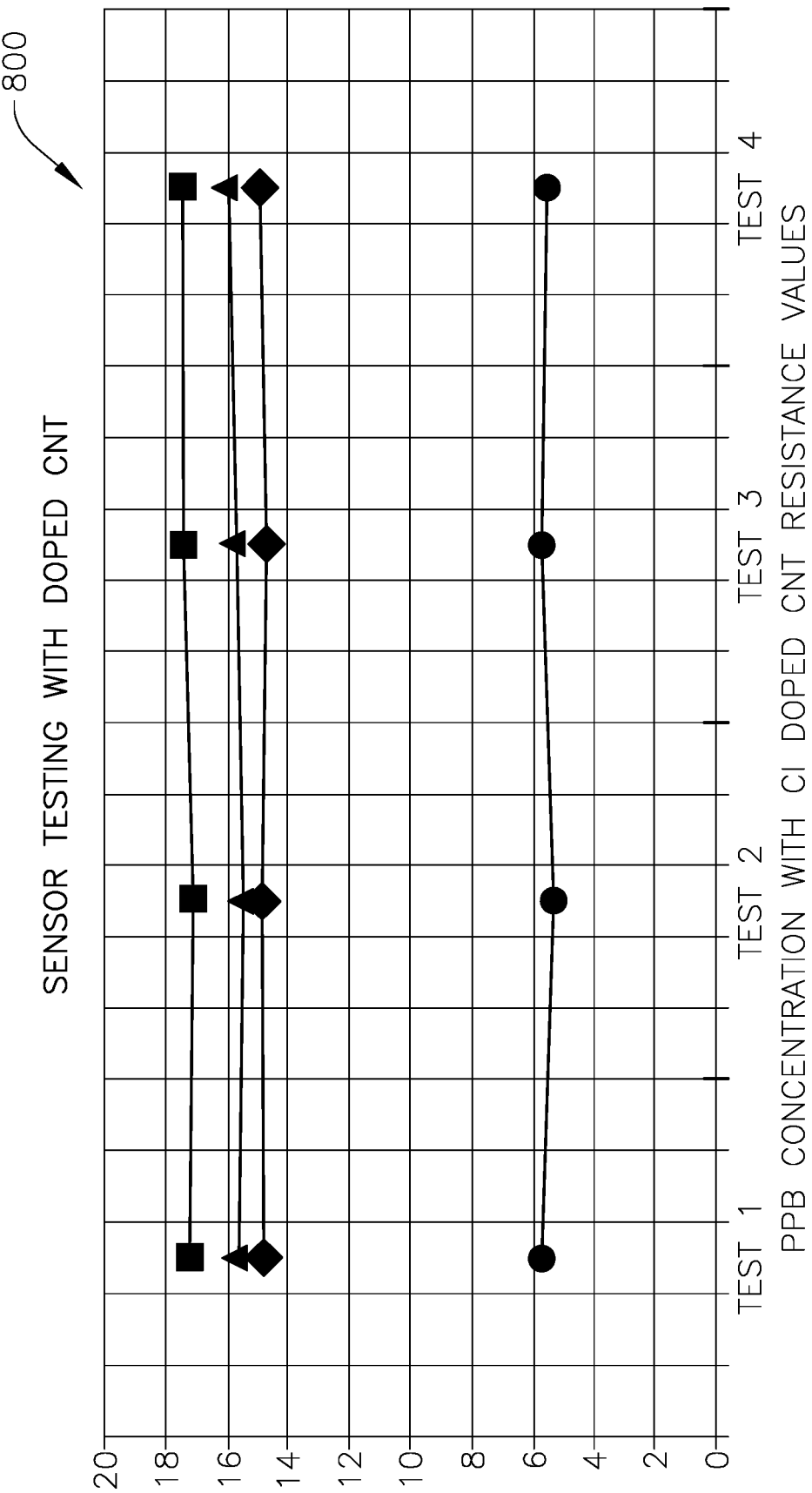
FIG. 8 illustrates resistance values of the device of FIG. 1 with carbon nanotubes of FIG. 2 with various concentrations of lead.

FIG. 8 illustrates the resistance values in the device 100 of FIG. 1 when sensor 111 of FIG. 2 is submerged into lead contaminated liquid. As shown in FIG. 7, the current flowing through the device 100 is inversely proportional to the percentage of lead contamination in the water, as the current values of the device 100 is highest with the lowest (e.g., 1%) concentration of the contaminant lead acetate in the liquid and the current values of the device 100 is lowest with the highest (e.g., 5%) concentration of the contaminant lead acetate in the liquid.

Figure 9:
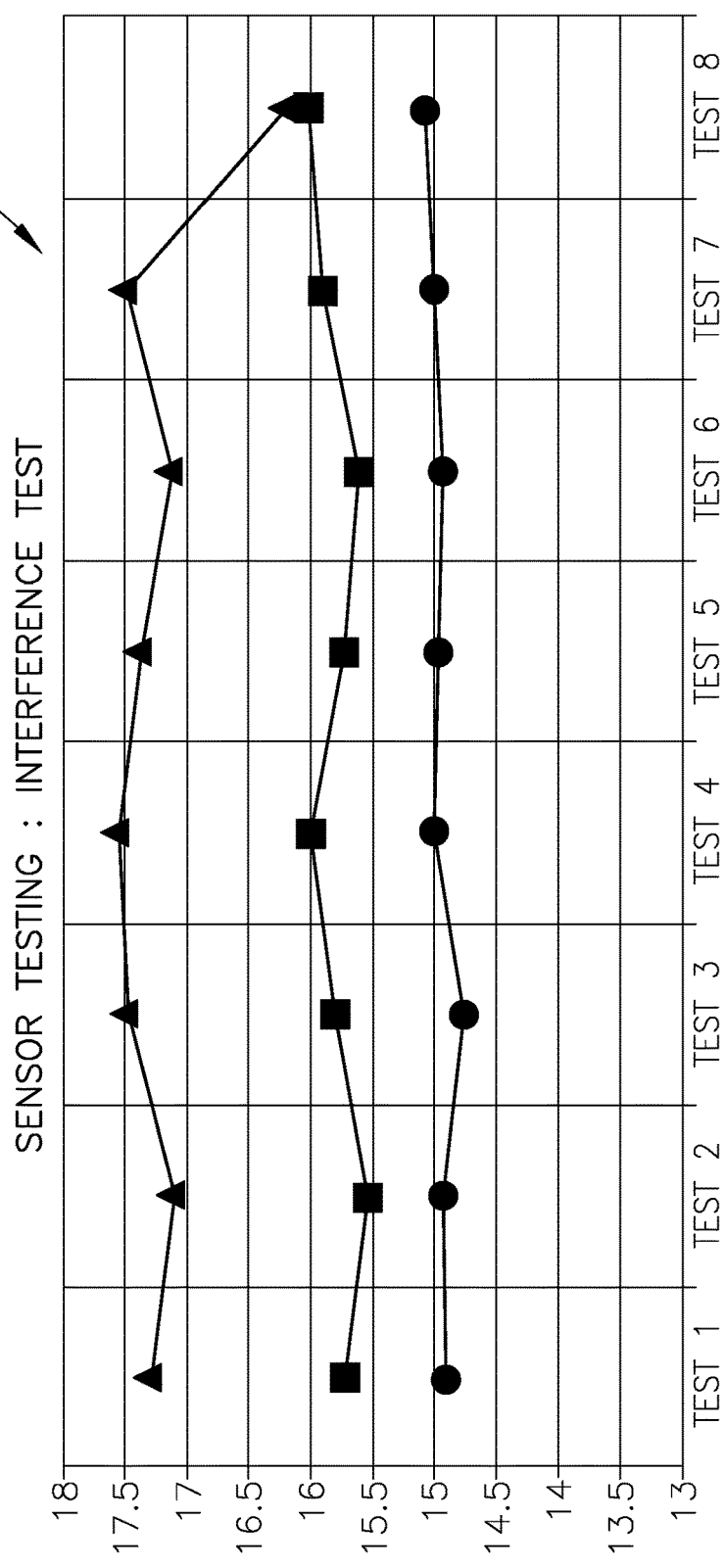
FIG. 9 illustrates the resistance values of the device of FIG. 1 with interferences from Chloride-Fluoride mixture.

FIG. 9 illustrates the resistance values of the device 100 of FIG. 1 when various interferences are added to the mixture when the sensor 111 is submerged into a lead, chloride, and fluoride contaminated liquid. As shown in FIG. 9, the resistance of the device 100 is directly correlated to the percentage of lead contamination in the water, as the resistance of the device 100 is highest (e.g., between 16 ohms and 17.5 ohms) with the highest (e.g., 15 ppb lead) concentration of the contaminant in the liquid and the resistance of the device 100 is lowest (e.g., between 14.5 ohms and 13 ohms) with the lowest (e.g., 5 ppb lead) concentration of the contaminant lead acetate in the liquid.

It will be understood that, although the terms "first", "second", "third", etc., may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed herein could be termed a second element, component, region, layer or section, without departing from the spirit and scope of the inventive concept.

Spatially relative terms, such as "beneath", "below", "lower", "under", "above", "upper" and the like, may be used herein for ease of description to describe one element or feature's relationship to another element(s) or feature(s) as illustrated in the figures. It will be understood that such spatially relative terms are intended to encompass different orientations of the device in use or in operation, in addition to the orientation depicted in the figures. For example, if the device in the figures is turned over, elements described as "below" or "beneath" or "under" other elements or features would then be oriented "above" the other elements or features. Thus, the example terms "below" and "under" can encompass both an orientation of above and below. The device may be otherwise oriented (e.g., rotated 90 degrees or at other orientations) and the spatially relative descriptors used herein should be interpreted accordingly. In addition, it will also be understood that when a layer is referred to as being "between" two layers, it can be the only layer between the two layers, or one or more intervening layers may also be present.

The terminology used herein is for the purpose of describing particular embodiments only and is not intended to be limiting of the inventive concept. As used herein, the terms "substantially," "about," and similar terms are used as terms of approximation and not as terms of degree, and are intended to account for the inherent deviations in measured or calculated values that would be recognized by those of ordinary skill in the art.

As used herein, the singular forms "a" and "an" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Further, the use of "may" when describing embodiments of the inventive concept refers to "one or more embodiments of the present invention". Also, the term "exemplary" is intended to refer to an example or illustration. As used herein, the terms "use," "using," and "used" may be considered synonymous with the terms "utilize," "utilizing," and "utilized," respectively.

It will be understood that when an element or layer is referred to as being "on", "connected to", "coupled to", or "adjacent to" another element or layer, it may be directly on, connected to, coupled to, or adjacent to the other element or layer, or one or more intervening elements or layers may be present. In contrast, when an element or layer is referred to as being "directly on", "directly connected to", "directly coupled to", or "immediately adjacent to" another element or layer, there are no intervening elements or layers present.

Any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein.

The electronic or electric devices and/or any other relevant devices or components according to embodiments of the present invention described herein may be implemented utilizing any suitable hardware, firmware (e.g. an application-specific integrated circuit), software, or a combination of software, firmware, and hardware. For example, the various components of these devices may be formed on one integrated circuit (IC) chip or on separate IC chips. Further, the various components of these devices may be implemented on a flexible printed circuit film, a tape carrier package (TCP), a printed circuit board (PCB), or formed on one substrate. Further, the various components of these devices may be a process or thread, running on one or more processors, in one or more computing devices, executing computer program instructions and interacting with other system components for performing the various functionalities described herein. The computer program instructions are stored in a memory which may be implemented in a computing device using a standard memory device, such as, for example, a random access memory (RAM). The computer program instructions may also be stored in other non-transitory computer readable media such as, for example, a CD-ROM, flash drive, or the like. Also, a person of skill in the art should recognize that the functionality of various computing devices may be combined or integrated into a single computing device, or the functionality of a particular computing device may be distributed across one or more other computing devices without departing from the spirit and scope of the exemplary embodiments of the present invention.

Although some exemplary embodiments of a system and method for detecting contaminants (e.g., lead and lead based compounds) in water have been specifically described and illustrated herein, many modifications and variations will be apparent to those skilled in the art. For example, in one variation, a display or other indicator to provide information of the amount of contamination or level of safety of the water to a user may be included on the housing of the device or on the sensing device in addition to or as an alternate to that of the wireless device. Accordingly, it is to be understood that to a system and method for detecting contaminants (e.g., lead and lead based compounds) in water constructed according to principles of this invention may be embodied other than as specifically described herein. The invention is also defined in the following claims, and equivalents thereof.

What is claimed is:

1. A device comprising:
   a sensor configured to detect one or more contaminants in a liquid when the sensor is dipped into the liquid;
   a computing device connected to the sensor, the computing device being configured to determine a resistance of the device when the sensor is dipped into the liquid; and
   a wireless electronic device connected to the computing device via one or more wireless links and configured to receive the resistance of the device when the sensor is dipped into the liquid from the computing device,
   wherein the wireless electronic device determines a level of contamination in the liquid based on a difference between the resistance of the device when the sensor is dipped into the liquid and a set or predetermined resistance, and
   wherein the wireless electronic device is configured to determine if the level of contamination in the liquid is safe for drinking based on a result of a comparison between the difference and a first threshold.

2. The device of claim 1, wherein the sensor is a carbon nanotube sensor located inside an insulated cartridge with small opening to expose one or more carbon nanotubes in the carbon nanotube sensor.

3. The device of claim 2, wherein each of the one or more carbon nanotubes is a single walled carbon nanotube and has a single walled armchair design.

4. The device of claim 2, wherein the one or more carbon nanotubes are doped with one of chloride ions, iodide ions, or fluoride ions.

5. The device of claim 4, wherein an amount of chloride ions in each of the one or more carbon nanotubes is 5% of a total volume of the each of the one or more carbon nanotubes.

6. The device of claim 1, wherein the computing device is a microcontroller connected to the sensor via one or more resistors.

7. The device of claim 6, wherein the microcontroller determines the resistance of the device when the sensor is dipped into the liquid using the one or more resistors, the microcontroller being an Adafruit Feather 32u4 Bluefruit microcontroller.

8. The device of claim 6, wherein a 4.3V, 100 mA Lithium Polymer or Lithium Ion battery source is connected to the microcontroller to power the device.

9. The device of claim 6, wherein the one or more resistors are calibrated on scale of the one or more contaminants in the liquid.

10. A device comprising:
    a sensor configured to detect one or more contaminants in a liquid when the sensor is dipped into the liquid;
    a computing device connected to the sensor, the computing device being configured to determine a resistance of the device when the sensor is dipped into the liquid; and
    a wireless electronic device connected to the computing device via one or more wireless links and configured to receive the resistance of the device when the sensor is dipped into the liquid from the computing device,
    wherein the wireless electronic device determines a level of contamination in the liquid based on a difference between the resistance of the device when the sensor is dipped into the liquid and a set or predetermined resistance,
    wherein the computing device is a microcontroller connected to the sensor via one or more resistors,
    wherein the one or more resistors are calibrated on scale of the one or more contaminants in the liquid, and
    wherein the one or more resistors are calibrated on scale of lead acetate in lead contaminated water.

11. The device of claim 1, wherein the wireless electronic device is one of a smart phone, smart watch, tablet, computer, or the like.

12. The device of claim 1, wherein the set or predetermined resistance is a resistance of the device when the sensor is not dipped into the liquid, wherein the set or predetermined resistance is saved in a local memory of the wireless electronic device or in a remote server connected to the wireless electronic device.

13. The device of claim 1, wherein
if the difference between the resistance of the device when the sensor is dipped into the liquid and the set or predetermined resistance is less than or equal to the first threshold, the wireless electronic device determines that the level of contamination in the liquid is "safe" for drinking, and displays "safe" at a display screen of the wireless electronic device;
if the difference between the resistance of the device when the sensor is dipped into the liquid and the set or predetermined resistance is greater than the first threshold but less than or equal to a second threshold, the wireless electronic device determines that the level of contamination in the liquid is at "moderate risk" for drinking, and displays "moderate risk" at the display screen of the wireless electronic device; and
if the difference between the resistance of the device when the sensor is dipped into the liquid and the set or predetermined resistance is greater than the second threshold, the wireless electronic device determines that the level of contamination in the liquid is "unsafe" for drinking, and displays "unsafe" at the display screen of the wireless electronic device.

14. A method for detecting contaminants in liquid, the method comprising:
submerging a sensor connected to a device into a liquid;
determining, using a processor in the device, a resistance of the device when the sensor is submerged into the liquid;
determining, at a wireless electronic device connected to the processor via one or more wireless links, a difference between the resistance of the device when the sensor is submerged into the liquid and a set or predetermined resistance;
determining a level of contamination in the liquid based on the difference between the resistance of the device when the sensor is submerged into the liquid and the set or predetermined resistance; and
determining if the level of contamination in the liquid is safe for drinking based on a result of a comparison between the difference and a first threshold.

15. The method of claim 14, wherein the sensor is a carbon nanotube based sensor.

16. The method of claim 15, wherein one or more carbon nanotubes in the carbon nanotube based sensor are doped with one of chloride ions, iodide ions, or fluoride ions.

17. The method of claim 14, wherein the processor is a microcontroller connected to the sensor via one or more resistors, wherein the microcontroller determines the resistance of the device when the sensor is submerged into the liquid using the one or more resistors, the microcontroller being an Adafruit Feather 32u4 Bluefruit microcontroller.

18. The method of claim 14, wherein
if the difference between the resistance of the device when the sensor is submerged into the liquid and the set or predetermined resistance is less than or equal to the first threshold, the wireless electronic device determines that the level of contamination in the liquid is "safe" for drinking, and displays "safe" at a display screen of the wireless electronic device;
if the difference between the resistance of the device when the sensor is submerged into the liquid and the set or predetermined resistance is greater than the first threshold but less than or equal to a second threshold, the wireless electronic device determines that the level of contamination in the liquid is at "moderate risk" for drinking, and displays "moderate risk" at the display screen of the wireless electronic device; and
if the difference between the resistance of the device when the sensor is submerged into the liquid and the set or predetermined resistance is greater than the second threshold, the wireless electronic device determines that the level of contamination in the liquid is "unsafe" for drinking, and displays "unsafe" at the display screen of the wireless electronic device.

19. A system comprising:
a carbon nanotube sensor configured to detect one or more contaminants in a liquid when the carbon nanotube sensor is submerged into the liquid, wherein each of one or more carbon nanotubes in the carbon nanotube sensor is doped with one of chloride ions, iodide ions, or fluoride ions;
a microcontroller connected to the carbon nanotube sensor via one or more resistors, wherein the microcontroller is configured to determine a resistance of the system when the carbon nanotube sensor is submerged into the liquid, using the one or more resistors; and
a wireless electronic device connected to the microcontroller via one or more wireless links and configured to receive the resistance of the system when the carbon nanotube sensor is submerged into the liquid from the microcontroller,
wherein the wireless electronic device determines a level of contamination in the liquid based on a difference between the resistance of the system when the carbon nanotube sensor is submerged into the liquid and a set or predetermined resistance, and
wherein the wireless electronic device is configured to determine if the level of contamination in the liquid is safe for drinking based on a result of a comparison between the difference and a first threshold.

20. The system of claim 19, wherein the set or predetermined resistance is a resistance of the system when the carbon nanotube sensor is not submerged into the liquid, wherein the set or predetermined resistance is saved in a local memory of the wireless electronic device or in a remote server connected to the wireless electronic device.

* * * * *